(12) United States Patent
Chin

(10) Patent No.: US 8,437,826 B2
(45) Date of Patent: *May 7, 2013

(54) CLIP-STYLE MEDICAL SENSOR AND TECHNIQUE FOR USING THE SAME

(75) Inventor: Rodney P. Chin, Carson City, NV (US)

(73) Assignee: Covidien LP, Mansfield, MA (US)

( * ) Notice: Subject to any disclaimer, the term of this patent is extended or adjusted under 35 U.S.C. 154(b) by 9 days.

This patent is subject to a terminal disclaimer.

(21) Appl. No.: 13/290,957

(22) Filed: Nov. 7, 2011

(65) Prior Publication Data

US 2012/0053435 A1  Mar. 1, 2012

Related U.S. Application Data

(63) Continuation of application No. 11/415,717, filed on May 2, 2006, now Pat. No. 8,073,518.

(51) Int. Cl.
*A61B 5/1455* (2006.01)

(52) U.S. Cl.
USPC ............ 600/344; 600/310; 600/322; 600/323

(58) Field of Classification Search .................. 600/310, 600/322, 323, 340, 344, 473, 476; 356/41
See application file for complete search history.

(56) References Cited

U.S. PATENT DOCUMENTS

| | | | |
|---|---|---|---|
| 3,403,555 A | 10/1968 | Versaci et al. | |
| 3,536,545 A | 10/1970 | Traynor et al. | |
| D222,454 S | 10/1971 | Beeber | |
| 3,628,525 A | 12/1971 | Polanyi et al. | |
| 3,721,813 A | 3/1973 | Condon et al. | |
| 3,810,460 A | 5/1974 | Van Nie et al. | |
| 3,815,607 A | 6/1974 | Chester | |
| 4,098,772 A | 7/1978 | Bonk et al. | |
| D250,275 S | 11/1978 | Bond | |
| D251,387 S | 3/1979 | Ramsay et al. | |
| D262,488 S | 12/1981 | Rossman et al. | |
| 4,321,930 A | 3/1982 | Jobsis et al. | |
| 4,334,544 A | 6/1982 | Hill et al. | |
| 4,350,165 A | 9/1982 | Striese | |
| 4,353,372 A | 10/1982 | Ayer | |
| 4,380,240 A | 4/1983 | Jobsis et al. | |
| 4,406,289 A | 9/1983 | Wesseling et al. | |

(Continued)

FOREIGN PATENT DOCUMENTS

| | | |
|---|---|---|
| CN | 11080192 | 11/2007 |
| DE | 263522 | 2/1978 |

(Continued)

OTHER PUBLICATIONS

Yamazaki, Nakaji, et al.; "Motion Artifact Resistant Pulse Oximeter (Durapulse PA 2100)," Journal of Oral Cavity Medicine, vol. 69, No. 4, pp. 53 (1980) (Article in Japanese—contains English summary of article).

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

A clip-style pulse sensor may be adapted to apply limited, even pressure to a patient's tissue. A clip-style sensor is provided that reduces motion artifacts by exerting limited, uniform pressure to the patient tissue to reduce tissue exsanguination. Further, such a sensor provides a secure fit while avoiding discomfort for the wearer.

20 Claims, 5 Drawing Sheets

U.S. PATENT DOCUMENTS

| | | |
|---|---|---|
| 4,510,551 A | 4/1985 | Brainard, II |
| 4,510,938 A | 4/1985 | Jobsis et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick et al. |
| 5,349,519 A | 9/1994 | Kaestle |
| 5,349,952 A | 9/1994 | McCarthy et al. |
| 5,349,953 A | 9/1994 | McCarthy et al. |

| | | | | | |
|---|---|---|---|---|---|
| 5,351,685 A | 10/1994 | Potratz | 5,596,986 A | 1/1997 | Goldfarb |
| 5,353,799 A | 10/1994 | Chance | 5,611,337 A | 3/1997 | Bukta |
| 5,355,880 A | 10/1994 | Thomas et al. | 5,617,852 A | 4/1997 | MacGregor |
| 5,355,882 A | 10/1994 | Ukawa et al. | 5,619,991 A | 4/1997 | Sloane |
| 5,361,758 A | 11/1994 | Hall et al. | 5,619,992 A | 4/1997 | Guthrie et al. |
| 5,365,066 A | 11/1994 | Krueger, Jr. et al. | 5,626,140 A | 5/1997 | Feldman et al. |
| 5,368,025 A | 11/1994 | Young et al. | 5,630,413 A | 5/1997 | Thomas et al. |
| 5,368,026 A | 11/1994 | Swedlow et al. | 5,632,272 A | 5/1997 | Diab et al. |
| 5,368,224 A | 11/1994 | Richardson et al. | 5,632,273 A | 5/1997 | Suzuki |
| 5,372,136 A | 12/1994 | Steuer et al. | 5,634,459 A | 6/1997 | Gardosi |
| 5,377,675 A | 1/1995 | Ruskewicz et al. | 5,638,593 A | 6/1997 | Gerhardt et al. |
| 5,385,143 A | 1/1995 | Aoyagi | 5,638,816 A | 6/1997 | Kiani-Azarbayjany et al. |
| 5,387,122 A | 2/1995 | Goldberger et al. | 5,638,818 A | 6/1997 | Diab et al. |
| 5,390,670 A | 2/1995 | Centa et al. | 5,645,060 A | 7/1997 | Yorkey et al. |
| 5,392,777 A | 2/1995 | Swedlow et al. | 5,645,440 A | 7/1997 | Tobler et al. |
| 5,398,680 A | 3/1995 | Polson et al. | 5,660,567 A | 8/1997 | Nierlich et al. |
| 5,402,777 A | 4/1995 | Warring et al. | 5,662,105 A | 9/1997 | Tien |
| 5,402,779 A | 4/1995 | Chen et al. | 5,662,106 A | 9/1997 | Swedlow et al. |
| 5,411,023 A | 5/1995 | Morris, Sr. et al. | 5,664,270 A | 9/1997 | Bell et al. |
| 5,411,024 A | 5/1995 | Thomas et al. | 5,666,952 A | 9/1997 | Fuse et al. |
| 5,413,099 A | 5/1995 | Schmidt et al. | 5,671,529 A | 9/1997 | Nelson |
| 5,413,100 A | 5/1995 | Barthelemy et al. | 5,673,692 A | 10/1997 | Schulze et al. |
| 5,413,101 A | 5/1995 | Sugiura | 5,673,693 A | 10/1997 | Solenberger |
| 5,413,102 A | 5/1995 | Schmidt et al. | 5,676,139 A | 10/1997 | Goldberger et al. |
| 5,417,207 A | 5/1995 | Young et al. | 5,676,141 A | 10/1997 | Hollub |
| 5,421,329 A | 6/1995 | Casciani et al. | 5,678,544 A | 10/1997 | DeLonzor et al. |
| 5,425,360 A | 6/1995 | Nelson | 5,680,857 A | 10/1997 | Pelikan et al. |
| 5,425,362 A | 6/1995 | Siker et al. | 5,685,299 A | 11/1997 | Diab et al. |
| 5,427,093 A | 6/1995 | Ogawa et al. | 5,685,301 A | 11/1997 | Klomhaus |
| 5,429,128 A | 7/1995 | Cadell et al. | 5,687,719 A | 11/1997 | Sato et al. |
| 5,429,129 A | 7/1995 | Lovejoy et al. | 5,687,722 A | 11/1997 | Tien et al. |
| 5,431,159 A | 7/1995 | Baker et al. | 5,692,503 A | 12/1997 | Kuenstner |
| 5,431,170 A | 7/1995 | Mathews | 5,692,505 A | 12/1997 | Fouts |
| 5,437,275 A | 8/1995 | Amundsen et al. | 5,709,205 A | 1/1998 | Bukta |
| 5,438,986 A | 8/1995 | Disch et al. | 5,713,355 A | 2/1998 | Richardson et al. |
| 5,448,991 A | 9/1995 | Polson et al. | 5,724,967 A | 3/1998 | Venkatachalam |
| 5,452,717 A | 9/1995 | Branigan et al. | 5,727,547 A | 3/1998 | Levinson et al. |
| 5,465,714 A | 11/1995 | Scheuing | 5,730,124 A | 3/1998 | Yamauchi |
| 5,469,845 A | 11/1995 | DeLonzor et al. | 5,731,582 A | 3/1998 | West |
| RE35,122 E | 12/1995 | Corenman et al. | D393,830 S | 4/1998 | Tobler et al. |
| 5,482,034 A | 1/1996 | Lewis et al. | 5,743,260 A | 4/1998 | Chung et al. |
| 5,482,036 A | 1/1996 | Diab et al. | 5,743,262 A | 4/1998 | Lepper, Jr. et al. |
| 5,485,847 A | 1/1996 | Baker, Jr. | 5,743,263 A | 4/1998 | Baker, Jr. |
| 5,490,505 A | 2/1996 | Diab et al. | 5,746,206 A | 5/1998 | Mannheimer |
| 5,490,523 A | 2/1996 | Isaacson et al. | 5,746,697 A | 5/1998 | Swedlow et al. |
| 5,491,299 A | 2/1996 | Naylor et al. | 5,752,914 A | 5/1998 | DeLonzor et al. |
| 5,494,032 A | 2/1996 | Robinson et al. | 5,755,226 A | 5/1998 | Carim et al. |
| 5,494,043 A | 2/1996 | O'Sullivan et al. | 5,758,644 A | 6/1998 | Diab et al. |
| 5,497,771 A | 3/1996 | Rosenheimer | 5,760,910 A | 6/1998 | Lepper, Jr. et al. |
| 5,499,627 A | 3/1996 | Steuer et al. | 5,766,125 A | 6/1998 | Aoyagi et al. |
| 5,503,148 A | 4/1996 | Pologe et al. | 5,766,127 A | 6/1998 | Pologe et al. |
| 5,505,199 A | 4/1996 | Kim | 5,769,785 A | 6/1998 | Diab et al. |
| 5,507,286 A | 4/1996 | Solenberger | 5,772,587 A | 6/1998 | Gratton et al. |
| 5,511,546 A | 4/1996 | Hon | 5,774,213 A | 6/1998 | Trebino et al. |
| 5,517,988 A | 5/1996 | Gerhard | 5,776,058 A | 7/1998 | Levinson et al. |
| 5,520,177 A | 5/1996 | Ogawa et al. | 5,776,059 A | 7/1998 | Kaestle et al. |
| 5,521,851 A | 5/1996 | Wei et al. | 5,779,630 A | 7/1998 | Fein et al. |
| 5,522,388 A | 6/1996 | Ishikawa et al. | 5,779,631 A | 7/1998 | Chance |
| 5,524,617 A | 6/1996 | Mannheimer | 5,782,237 A | 7/1998 | Casciani et al. |
| 5,529,064 A | 6/1996 | Rall et al. | 5,782,756 A | 7/1998 | Mannheimer |
| 5,533,507 A | 7/1996 | Potratz et al. | 5,782,757 A | 7/1998 | Diab et al. |
| 5,551,259 A | 9/1996 | Calabro | 5,782,758 A | 7/1998 | Ausec et al. |
| 5,551,423 A | 9/1996 | Sugiura | 5,786,592 A | 7/1998 | Hök |
| 5,551,424 A | 9/1996 | Morrison et al. | 5,788,634 A | 8/1998 | Suda et al. |
| 5,553,614 A | 9/1996 | Chance | 5,790,729 A | 8/1998 | Pologe et al. |
| 5,553,615 A | 9/1996 | Carim et al. | 5,792,052 A | 8/1998 | Isaacson et al. |
| 5,555,882 A | 9/1996 | Richardson et al. | 5,795,292 A | 8/1998 | Lewis et al. |
| 5,558,096 A | 9/1996 | Palatnik | 5,797,841 A | 8/1998 | DeLonzor et al. |
| 5,560,355 A | 10/1996 | Merchant et al. | 5,800,348 A | 9/1998 | Kaestle |
| 5,564,417 A | 10/1996 | Chance | 5,800,349 A | 9/1998 | Isaacson et al. |
| 5,575,284 A | 11/1996 | Athan et al. | 5,803,910 A | 9/1998 | Potratz |
| 5,575,285 A | 11/1996 | Takanashi et al. | 5,807,246 A | 9/1998 | Sakaguchi et al. |
| 5,577,500 A | 11/1996 | Potratz | 5,807,247 A | 9/1998 | Merchant et al. |
| 5,582,169 A | 12/1996 | Oda et al. | 5,807,248 A | 9/1998 | Mills |
| 5,584,296 A | 12/1996 | Cui et al. | 5,810,723 A | 9/1998 | Aldrich |
| 5,588,425 A | 12/1996 | Sackner et al. | 5,810,724 A | 9/1998 | Gronvall |
| 5,588,427 A | 12/1996 | Tien | 5,813,980 A | 9/1998 | Levinson et al. |
| 5,590,652 A | 1/1997 | Inai | 5,817,008 A | 10/1998 | Rafert et al. |
| 5,595,176 A | 1/1997 | Yamaura | 5,817,009 A | 10/1998 | Rosenheimer et al. |

| Patent | Kind | Date | Inventor |
|---|---|---|---|
| 5,817,010 | A | 10/1998 | Hibl |
| 5,818,985 | A | 10/1998 | Merchant et al. |
| 5,820,550 | A | 10/1998 | Polson et al. |
| 5,823,950 | A | 10/1998 | Diab et al. |
| 5,823,952 | A | 10/1998 | Levinson et al. |
| 5,827,179 | A | 10/1998 | Lichter et al. |
| 5,827,182 | A | 10/1998 | Raley et al. |
| 5,829,439 | A | 11/1998 | Yokosawa et al. |
| 5,830,135 | A | 11/1998 | Bosque et al. |
| 5,830,136 | A | 11/1998 | DeLonzor et al. |
| 5,830,137 | A | 11/1998 | Scharf |
| 5,839,439 | A | 11/1998 | Nierlich et al. |
| RE36,000 | E | 12/1998 | Swedlow et al. |
| 5,842,979 | A | 12/1998 | Jarman et al. |
| 5,842,981 | A | 12/1998 | Larsen et al. |
| 5,842,982 | A | 12/1998 | Mannheimer |
| 5,846,190 | A | 12/1998 | Woehrle |
| 5,851,178 | A | 12/1998 | Aronow |
| 5,851,179 | A | 12/1998 | Ritson et al. |
| 5,853,364 | A | 12/1998 | Baker, Jr. et al. |
| 5,860,919 | A | 1/1999 | Kiani-Azarbayjany et al. |
| 5,865,736 | A | 2/1999 | Baker, Jr. et al. |
| 5,879,294 | A | 3/1999 | Anderson et al. |
| 5,885,213 | A | 3/1999 | Richardson et al. |
| 5,890,929 | A | 4/1999 | Mills et al. |
| 5,891,021 | A | 4/1999 | Dillon et al. |
| 5,891,022 | A | 4/1999 | Pologe |
| 5,891,024 | A | 4/1999 | Jarman et al. |
| 5,891,025 | A | 4/1999 | Buschmann et al. |
| 5,891,026 | A | 4/1999 | Wang et al. |
| 5,902,235 | A | 5/1999 | Lewis et al. |
| 5,910,108 | A | 6/1999 | Solenberger |
| 5,911,690 | A | 6/1999 | Rall |
| 5,912,656 | A | 6/1999 | Tham et al. |
| 5,913,819 | A | 6/1999 | Taylor et al. |
| 5,916,154 | A | 6/1999 | Hobbs et al. |
| 5,916,155 | A | 6/1999 | Levinson et al. |
| 5,919,133 | A | 7/1999 | Taylor et al. |
| 5,919,134 | A | 7/1999 | Diab |
| 5,920,263 | A | 7/1999 | Huttenhoff et al. |
| 5,921,921 | A | 7/1999 | Potratz et al. |
| 5,922,607 | A | 7/1999 | Bernreuter |
| 5,924,979 | A | 7/1999 | Swedlow et al. |
| 5,924,980 | A | 7/1999 | Coetzee |
| 5,924,982 | A | 7/1999 | Chin |
| 5,924,985 | A | 7/1999 | Jones |
| 5,934,277 | A | 8/1999 | Mortz |
| 5,934,925 | A | 8/1999 | Tobler et al. |
| 5,940,182 | A | 8/1999 | Lepper, Jr. et al. |
| 5,954,644 | A | 9/1999 | Dettling et al. |
| 5,957,840 | A | 9/1999 | Terasawa et al. |
| 5,960,610 | A | 10/1999 | Levinson et al. |
| 5,961,450 | A | 10/1999 | Merchant et al. |
| 5,961,452 | A | 10/1999 | Chung et al. |
| 5,964,701 | A | 10/1999 | Asada et al. |
| 5,971,930 | A | 10/1999 | Elghazzawi |
| 5,978,691 | A | 11/1999 | Mills |
| 5,978,693 | A | 11/1999 | Hamilton et al. |
| 5,983,120 | A | 11/1999 | Groner et al. |
| 5,983,122 | A | 11/1999 | Jarman et al. |
| 5,987,343 | A | 11/1999 | Kinast |
| 5,991,648 | A | 11/1999 | Levin |
| 5,995,855 | A | 11/1999 | Kiani et al. |
| 5,995,856 | A | 11/1999 | Mannheimer et al. |
| 5,995,858 | A | 11/1999 | Kinast |
| 5,995,859 | A | 11/1999 | Takahashi |
| 5,997,343 | A | 12/1999 | Mills et al. |
| 5,999,834 | A | 12/1999 | Wang et al. |
| 6,002,952 | A | 12/1999 | Diab et al. |
| 6,005,658 | A | 12/1999 | Kaluza et al. |
| 6,006,120 | A | 12/1999 | Levin |
| 6,011,985 | A | 1/2000 | Athan et al. |
| 6,011,986 | A | 1/2000 | Diab et al. |
| 6,014,576 | A | 1/2000 | Raley |
| 6,018,673 | A | 1/2000 | Chin et al. |
| 6,018,674 | A | 1/2000 | Aronow |
| 6,022,321 | A | 2/2000 | Amano et al. |
| 6,023,541 | A | 2/2000 | Merchant et al. |
| 6,026,312 | A | 2/2000 | Shemwell et al. |
| 6,026,314 | A | 2/2000 | Amerov et al. |
| 6,031,603 | A | 2/2000 | Fine et al. |
| 6,035,223 | A | 3/2000 | Baker, Jr. |
| 6,036,642 | A | 3/2000 | Diab et al. |
| 6,041,247 | A | 3/2000 | Weckstrom et al. |
| 6,044,283 | A | 3/2000 | Fein et al. |
| 6,047,201 | A | 4/2000 | Jackson, III |
| 6,055,447 | A | 4/2000 | Weil |
| 6,061,584 | A | 5/2000 | Lovejoy et al. |
| 6,064,898 | A | 5/2000 | Aldrich |
| 6,064,899 | A | 5/2000 | Fein et al. |
| 6,067,462 | A | 5/2000 | Diab et al. |
| 6,073,038 | A | 6/2000 | Wang et al. |
| 6,078,829 | A | 6/2000 | Uchida |
| 6,078,833 | A | 6/2000 | Hueber |
| 6,081,735 | A | 6/2000 | Diab et al. |
| 6,083,157 | A | 7/2000 | Noller |
| 6,083,172 | A | 7/2000 | Baker, Jr. et al. |
| 6,088,607 | A | 7/2000 | Diab et al. |
| 6,094,592 | A | 7/2000 | Yorkey et al. |
| 6,095,974 | A | 8/2000 | Shemwell et al. |
| 6,104,938 | A | 8/2000 | Huiku et al. |
| 6,104,939 | A | 8/2000 | Groner |
| 6,112,107 | A | 8/2000 | Hannula |
| 6,113,541 | A | 9/2000 | Dias et al. |
| 6,115,621 | A | 9/2000 | Chin |
| 6,122,535 | A | 9/2000 | Kaestle et al. |
| 6,133,994 | A | 10/2000 | Mathews et al. |
| 6,135,952 | A | 10/2000 | Coetzee |
| 6,144,444 | A | 11/2000 | Haworth et al. |
| 6,144,867 | A | 11/2000 | Walker et al. |
| 6,144,868 | A | 11/2000 | Parker |
| 6,147,850 | A | 11/2000 | Gronowicz, Jr. |
| 6,149,481 | A | 11/2000 | Wang et al. |
| 6,151,107 | A | 11/2000 | Schöllermann et al. |
| 6,151,516 | A | 11/2000 | Kiani-Azarbayjany et al. |
| 6,151,518 | A | 11/2000 | Hayashi |
| 6,152,754 | A | 11/2000 | Gerhardt et al. |
| 6,154,667 | A | 11/2000 | Miura et al. |
| 6,157,850 | A | 12/2000 | Diab et al. |
| 6,159,147 | A | 12/2000 | Lichter |
| 6,159,850 | A | 12/2000 | Lee et al. |
| 6,163,175 | A | 12/2000 | Sharpe-Geisler |
| 6,163,715 | A | 12/2000 | Larsen et al. |
| 6,165,005 | A | 12/2000 | Mills et al. |
| 6,173,196 | B1 | 1/2001 | Delonzor et al. |
| 6,178,343 | B1 | 1/2001 | Bindszus et al. |
| 6,179,159 | B1 | 1/2001 | Gurley |
| 6,181,958 | B1 | 1/2001 | Steuer et al. |
| 6,181,959 | B1 | 1/2001 | Schöllermann et al. |
| 6,184,521 | B1 | 2/2001 | Coffin, IV et al. |
| 6,188,470 | B1 | 2/2001 | Grace |
| 6,192,260 | B1 | 2/2001 | Chance |
| 6,195,574 | B1 | 2/2001 | Kumar et al. |
| 6,195,575 | B1 | 2/2001 | Levinson |
| 6,198,951 | B1 | 3/2001 | Kosuda et al. |
| 6,206,830 | B1 | 3/2001 | Diab et al. |
| 6,213,952 | B1 | 4/2001 | Finarov et al. |
| 6,217,523 | B1 | 4/2001 | Amano et al. |
| 6,222,189 | B1 | 4/2001 | Misner et al. |
| 6,223,064 | B1 | 4/2001 | Lynn |
| 6,226,539 | B1 | 5/2001 | Potratz |
| 6,226,540 | B1 | 5/2001 | Bernreuter et al. |
| 6,229,856 | B1 | 5/2001 | Diab et al. |
| 6,230,035 | B1 | 5/2001 | Aoyagi et al. |
| 6,233,470 | B1 | 5/2001 | Tsuchiya |
| 6,236,871 | B1 | 5/2001 | Tsuchiya |
| 6,236,872 | B1 | 5/2001 | Diab et al. |
| 6,240,305 | B1 | 5/2001 | Tsuchiya |
| 6,253,097 | B1 | 6/2001 | Aronow et al. |
| 6,253,098 | B1 | 6/2001 | Walker et al. |
| 6,256,523 | B1 | 7/2001 | Diab et al. |
| 6,256,524 | B1 | 7/2001 | Walker et al. |
| 6,261,236 | B1 | 7/2001 | Grinblatov |
| 6,263,221 | B1 | 7/2001 | Chance et al. |
| 6,263,222 | B1 | 7/2001 | Diab et al. |
| 6,263,223 | B1 | 7/2001 | Sheperd et al. |
| 6,266,546 | B1 | 7/2001 | Steuer et al. |
| 6,266,547 | B1 | 7/2001 | Walker et al. |

| | | |
|---|---|---|
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddart et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,391,035 B1 | 5/2002 | Appleby et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| D458,226 S | 6/2002 | Chin |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Pishney et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |

| Patent | Date | Inventor |
|---|---|---|
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,967,652 B1 | 11/2005 | Nubling et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,112,175 B2 | 9/2006 | Gopinathan et al. |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,161,484 B2 | 1/2007 | Tsoukalis |
| 7,162,288 B2 | 1/2007 | Nordstrom et al. |
| 7,164,938 B2 | 1/2007 | Geddes et al. |
| 7,190,986 B1 | 3/2007 | Hannula et al. |
| 7,190,987 B2 | 3/2007 | Kindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,881 B2 | 6/2007 | Liu et al. |
| 7,245,953 B1 | 7/2007 | Parker |
| 7,248,910 B2 | 7/2007 | Li et al. |
| 7,254,433 B2 | 8/2007 | Diab et al. |
| 7,254,434 B2 | 8/2007 | Schulz et al. |
| 7,255,006 B2 | 8/2007 | Spanke et al. |
| 7,257,438 B2 | 8/2007 | Kinast |
| 7,263,396 B2 | 8/2007 | Chen et al. |
| 7,272,425 B2 | 9/2007 | Al-Ali |
| 7,280,858 B2 | 10/2007 | Al-Ali et al. |
| 7,292,150 B2 | 11/2007 | Shaw |
| 7,295,866 B2 | 11/2007 | Al-Ali |
| 7,297,119 B2 | 11/2007 | Westbrook et al. |
| 7,305,262 B2 | 12/2007 | Brodnick et al. |
| 7,315,753 B2 | 1/2008 | Baker, Jr. et al. |

| | | | | | | |
|---|---|---|---|---|---|---|
| 7,341,559 | B2 | 3/2008 | Schulz et al. | 2005/0070775 A1 | 3/2005 | Chin |
| 7,341,560 | B2 | 3/2008 | Henderson et al. | 2005/0075546 A1 | 4/2005 | Samsoondar |
| 7,359,741 | B2 | 4/2008 | Sarussi et al. | 2005/0075550 A1 | 4/2005 | Lindekugel |
| 7,359,742 | B2 | 4/2008 | Maser et al. | 2005/0085704 A1 | 4/2005 | Schulz |
| 7,412,272 | B2 | 8/2008 | Medina et al. | 2005/0090720 A1 | 4/2005 | Wu |
| 7,433,726 | B2 | 10/2008 | Perkins | 2005/0101851 A1 | 5/2005 | Chin |
| 7,435,222 | B2 | 10/2008 | Gopinathan et al. | 2005/0119538 A1 | 6/2005 | Jeon et al. |
| 2002/0016537 | A1 | 2/2002 | Muz et al. | 2005/0163412 A1 | 7/2005 | Glebov et al. |
| 2002/0026109 | A1 | 2/2002 | Diab et al. | 2005/0197548 A1 | 9/2005 | Dietiker |
| 2002/0028990 | A1 | 3/2002 | Shepherd et al. | 2005/0017864 A1 | 10/2005 | Banet |
| 2002/0038078 | A1 | 3/2002 | Ito | 2005/0228248 A1 | 10/2005 | Dietiker |
| 2002/0038082 | A1 | 3/2002 | Chin | 2005/0228299 A1 | 10/2005 | Banet |
| 2002/0042558 | A1 | 4/2002 | Mendelson | 2005/0228300 A1 | 10/2005 | Jaime et al. |
| 2002/0068859 | A1 | 6/2002 | Knopp | 2005/0256386 A1 | 11/2005 | Chan |
| 2002/0072681 | A1 | 6/2002 | Schnall | 2005/0272986 A1 | 12/2005 | Smith |
| 2002/0103423 | A1 | 8/2002 | Chin et al. | 2005/0277819 A1 | 12/2005 | Kiani et al. |
| 2002/0116797 | A1 | 8/2002 | Modgil et al. | 2005/0283082 A1 | 12/2005 | Geddes et al. |
| 2002/0128544 | A1 | 9/2002 | Diab et al. | 2006/0020179 A1 | 1/2006 | Anderson |
| 2002/0133067 | A1 | 9/2002 | Jackson, III | 2006/0030764 A1 | 2/2006 | Porges |
| 2002/0151775 | A1 | 10/2002 | Kondo | 2006/0036136 A1 | 2/2006 | Shaw |
| 2002/0156354 | A1 | 10/2002 | Larson | 2006/0058594 A1 | 3/2006 | Ishizuka et al. |
| 2002/0173706 | A1 | 11/2002 | Takatani | 2006/0058690 A1 | 3/2006 | Bartnik |
| 2002/0173709 | A1 | 11/2002 | Fine et al. | 2006/0064024 A1 | 3/2006 | Schnall |
| 2002/0190863 | A1 | 12/2002 | Lynn | 2006/0069319 A1 | 3/2006 | Elhag et al. |
| 2003/0018243 | A1 | 1/2003 | Gerhardt et al. | 2006/0074280 A1 | 4/2006 | Martis |
| 2003/0036690 | A1 | 2/2003 | Geddes et al. | 2006/0075257 A1 | 4/2006 | Martis et al. |
| 2003/0045785 | A1 | 3/2003 | Diab et al. | 2006/0079794 A1 | 4/2006 | Liu et al. |
| 2003/0073889 | A1 | 4/2003 | Keilbach et al. | 2006/0084852 A1 | 4/2006 | Mason et al. |
| 2003/0073890 | A1 | 4/2003 | Hanna | 2006/0084878 A1 | 4/2006 | Banet |
| 2003/0100840 | A1 | 5/2003 | Sugiura et al. | 2006/0089547 A1 | 4/2006 | Sarussi |
| 2003/0109775 | A1 | 6/2003 | O'Neil et al. | 2006/0106294 A1 | 5/2006 | Maser et al. |
| 2003/0171662 | A1 | 9/2003 | O'Connor et al. | 2006/0122517 A1 | 6/2006 | Banet |
| 2003/0181799 | A1 | 9/2003 | Lindekugel et al. | 2006/0129039 A1 | 6/2006 | Lindner |
| 2003/0187337 | A1 | 10/2003 | Tarassenko et al. | 2006/0149149 A1 | 7/2006 | Schmid |
| 2003/0197679 | A1 | 10/2003 | Ali et al. | 2006/0155198 A1 | 7/2006 | Schmid |
| 2003/0212316 | A1 | 11/2003 | Leiden et al. | 2006/0173257 A1 | 8/2006 | Nagai |
| 2003/0225323 | A1 | 12/2003 | Kiani et al. | 2006/0200018 A1 | 9/2006 | Al-Ali |
| 2004/0006261 | A1 | 1/2004 | Swedlow et al. | 2006/0253010 A1 | 11/2006 | Brady et al. |
| 2004/0024326 | A1 | 2/2004 | Yeo et al. | 2006/0276700 A1 | 12/2006 | O'Neil et al. |
| 2004/0039272 | A1 | 2/2004 | Abdul-Hafiz et al. | 2007/0021659 A1 | 1/2007 | Delonzor et al. |
| 2004/0039273 | A1 | 2/2004 | Terry | 2007/0021660 A1 | 1/2007 | Delonzor et al. |
| 2004/0044276 | A1 | 3/2004 | Arnold | 2007/0021662 A1 | 1/2007 | Delonzor et al. |
| 2004/0054291 | A1 | 3/2004 | Schulz et al. | 2007/0027376 A1 | 2/2007 | Todokoro et al. |
| 2004/0068164 | A1 | 4/2004 | Diab et al. | 2007/0027378 A1 | 2/2007 | Delonzor et al. |
| 2004/0092805 | A1 | 5/2004 | Yarita | 2007/0027379 A1 | 2/2007 | Delonzor et al. |
| 2004/0097797 | A1 | 5/2004 | Porges et al. | 2007/0027380 A1 | 2/2007 | Delonzor et al. |
| 2004/0098009 | A1 | 5/2004 | Boecker et al. | 2007/0032707 A1 | 2/2007 | Coakley et al. |
| 2004/0117891 | A1 | 6/2004 | Hannula et al. | 2007/0032708 A1 | 2/2007 | Eghbal et al. |
| 2004/0122302 | A1 | 6/2004 | Mason et al. | 2007/0032709 A1 | 2/2007 | Coakley et al. |
| 2004/0133088 | A1 | 7/2004 | Al-Ali | 2007/0032710 A1 | 2/2007 | Raridan et al. |
| 2004/0143172 | A1 | 7/2004 | Fudge et al. | 2007/0032711 A1 | 2/2007 | Coakley et al. |
| 2004/0147821 | A1 | 7/2004 | Al-Ali et al. | 2007/0032712 A1 | 2/2007 | Raridan et al. |
| 2004/0147824 | A1 | 7/2004 | Diab et al. | 2007/0032715 A1 | 2/2007 | Eghbal et al. |
| 2004/0158134 | A1 | 8/2004 | Diab et al. | 2007/0032716 A1 | 2/2007 | Raridan et al. |
| 2004/0162472 | A1 | 8/2004 | Berson et al. | 2007/0038050 A1 | 2/2007 | Sarussi |
| 2004/0167381 | A1 | 8/2004 | Lichter | 2007/0060808 A1 | 3/2007 | Hoarau |
| 2004/0186358 | A1 | 9/2004 | Chernow et al. | 2007/0073117 A1 | 3/2007 | Raridan |
| 2004/0199063 | A1 | 10/2004 | O'Neil et al. | 2007/0073121 A1 | 3/2007 | Hoarau et al. |
| 2004/0204637 | A1 | 10/2004 | Diab et al. | 2007/0073122 A1 | 3/2007 | Hoarau |
| 2004/0204638 | A1 | 10/2004 | Diab et al. | 2007/0073123 A1 | 3/2007 | Raridan |
| 2004/0204639 | A1 | 10/2004 | Casciani et al. | 2007/0073125 A1 | 3/2007 | Hoarau et al. |
| 2004/0204865 | A1 | 10/2004 | Lee et al. | 2007/0073126 A1 | 3/2007 | Raridan |
| 2004/0210146 | A1 | 10/2004 | Diab et al. | 2007/0073128 A1 | 3/2007 | Hoarau |
| 2004/0215085 | A1 | 10/2004 | Schnall | 2007/0078315 A1 | 4/2007 | Kling et al. |
| 2004/0236196 | A1 | 11/2004 | Diab et al. | 2007/0078316 A1 | 4/2007 | Hoarau |
| 2004/0257557 | A1 | 12/2004 | Block | 2007/0106132 A1 | 5/2007 | Elhag et al. |
| 2004/0260161 | A1 | 12/2004 | Melker et al. | 2007/0219440 A1 | 9/2007 | Hannula et al. |
| 2005/0004479 | A1 | 1/2005 | Townsend et al. | 2007/0260129 A1 | 11/2007 | Chin |
| 2005/0014999 | A1 | 1/2005 | Rahe-Meyer | 2007/0260130 A1 | 11/2007 | Chin |
| 2005/0020887 | A1 | 1/2005 | Goldberg | 2007/0260131 A1 | 11/2007 | Chin |
| 2005/0033131 | A1 | 2/2005 | Chen | 2007/0299328 A1 | 12/2007 | Chin et al. |
| 2005/0038050 | A1 | 2/2005 | Moore et al. | 2008/0009691 A1 | 1/2008 | Parker et al. |
| 2005/0043599 | A1 | 2/2005 | O'Mara | 2008/0200786 A1 | 8/2008 | Berndsen |
| 2005/0043600 | A1 | 2/2005 | Diab et al. | 2008/0262328 A1 | 10/2008 | Adams |
| 2005/0049468 | A1 | 3/2005 | Carlson | | | |
| 2005/0049471 | A1 | 3/2005 | Aceti et al. | | | |
| 2005/0059869 | A1 | 3/2005 | Scharf et al. | | | |
| 2005/0059870 | A1 | 3/2005 | Aceti | | | |
| 2005/0070773 | A1 | 3/2005 | Chin | | | |

FOREIGN PATENT DOCUMENTS

| | | |
|---|---|---|
| DE | 3405444 | 8/1985 |
| DE | 3516338 | 11/1986 |
| DE | 3703458 | 8/1988 |

| | | | | | |
|---|---|---|---|---|---|
| DE | 3938759 | 5/1991 | JP | 07236625 | 9/1995 |
| DE | 4210102 | 9/1993 | JP | 07246191 | 9/1995 |
| DE | 4423597 | 8/1995 | JP | 08256996 | 10/1996 |
| DE | 19632361 | 2/1997 | JP | 09192120 | 7/1997 |
| DE | 69123448 | 5/1997 | JP | 10216113 | 8/1998 |
| DE | 19703220 | 7/1997 | JP | 10216114 | 8/1998 |
| DE | 19640807 | 9/1997 | JP | 10216115 | 8/1998 |
| DE | 19647877 | 4/1998 | JP | 10337282 | 12/1998 |
| DE | 10030862 | 1/2002 | JP | 11019074 | 1/1999 |
| DE | 20318882 | 4/2004 | JP | 11155841 | 6/1999 |
| EP | 0127947 | 5/1984 | JP | 11188019 | 7/1999 |
| EP | 00194105 | 9/1986 | JP | 11244268 | 9/1999 |
| EP | 0204459 | 12/1986 | JP | 20107157 | 4/2000 |
| EP | 0262779 | 4/1988 | JP | 20237170 | 9/2000 |
| EP | 0315040 | 10/1988 | JP | 21245871 | 9/2001 |
| EP | 0314331 | 5/1989 | JP | 22224088 | 8/2002 |
| EP | 00352923 | 1/1990 | JP | 22282242 | 10/2002 |
| EP | 0360977 | 4/1990 | JP | 23153881 | 5/2003 |
| EP | 0430340 | 6/1991 | JP | 23153882 | 5/2003 |
| EP | 0435500 | 7/1991 | JP | 23169791 | 6/2003 |
| EP | 0572684 | 5/1992 | JP | 23194714 | 7/2003 |
| EP | 00497021 | 8/1992 | JP | 23210438 | 7/2003 |
| EP | 0529412 | 8/1992 | JP | 23275192 | 9/2003 |
| EP | 0531631 | 9/1992 | JP | 23339678 | 12/2003 |
| EP | 0566354 | 4/1993 | JP | 24008572 | 1/2004 |
| EP | 0587009 | 8/1993 | JP | 24089546 | 3/2004 |
| EP | 00630203 | 9/1993 | JP | 24113353 | 4/2004 |
| EP | 00615723 | 9/1994 | JP | 24135854 | 5/2004 |
| EP | 00702931 | 3/1996 | JP | 24148069 | 5/2004 |
| EP | 00724860 | 8/1996 | JP | 24148070 | 5/2004 |
| EP | 00793942 | 9/1997 | JP | 24159810 | 6/2004 |
| EP | 0864293 | 9/1998 | JP | 24166775 | 6/2004 |
| EP | 01006863 | 10/1998 | JP | 24194908 | 7/2004 |
| EP | 01006864 | 10/1998 | JP | 24202190 | 7/2004 |
| EP | 0875199 | 11/1998 | JP | 24248819 | 9/2004 |
| EP | 0998214 | 12/1998 | JP | 24248820 | 9/2004 |
| EP | 0898933 | 3/1999 | JP | 24261364 | 9/2004 |
| EP | 01332713 | 8/2003 | JP | 24290412 | 10/2004 |
| EP | 01469773 | 8/2003 | JP | 24290544 | 10/2004 |
| EP | 1502529 | 7/2004 | JP | 24290545 | 10/2004 |
| EP | 1491135 | 12/2004 | JP | 24329406 | 11/2004 |
| EP | 1807001 | 7/2007 | JP | 24329607 | 11/2004 |
| FR | 2685865 | 1/1992 | JP | 24329928 | 11/2004 |
| GB | 2259545 | 3/1993 | JP | 24337605 | 12/2004 |
| JP | 63275325 | 11/1988 | JP | 24344367 | 12/2004 |
| JP | 2013450 | 1/1990 | JP | 24351107 | 12/2004 |
| JP | 2111343 | 4/1990 | JP | 25034472 | 2/2005 |
| JP | 2191434 | 7/1990 | JP | 25052385 | 3/2005 |
| JP | 2237544 | 9/1990 | JP | 25110816 | 4/2005 |
| JP | 3170866 | 7/1991 | JP | 25111161 | 4/2005 |
| JP | 03173536 | 7/1991 | JP | 25125106 | 5/2005 |
| JP | 3245042 | 10/1991 | JP | 25168600 | 6/2005 |
| JP | 4174648 | 6/1992 | JP | 26122458 | 5/2006 |
| JP | 4191642 | 7/1992 | JP | 26122693 | 5/2006 |
| JP | 4332536 | 11/1992 | JP | 26158555 | 6/2006 |
| JP | 3124073 | 3/1993 | JP | 26212161 | 8/2006 |
| JP | 5049624 | 3/1993 | JP | 3818211 | 9/2006 |
| JP | 5049625 | 3/1993 | JP | 27020836 | 2/2007 |
| JP | 3115374 | 4/1993 | JP | 4038280 | 1/2008 |
| JP | 05212016 | 8/1993 | WO | WO9001293 | 2/1990 |
| JP | 25200031 | 8/1993 | WO | WO9004352 | 5/1990 |
| JP | 06014906 | 1/1994 | WO | WO9101678 | 2/1991 |
| JP | 06016774 | 3/1994 | WO | WO9111137 | 8/1991 |
| JP | 3116255 | 4/1994 | WO | WO9200513 | 1/1992 |
| JP | 06029504 | 4/1994 | WO | WO9221281 | 12/1992 |
| JP | 06098881 | 4/1994 | WO | WO9309711 | 5/1993 |
| JP | 06154177 | 6/1994 | WO | WO9313706 | 7/1993 |
| JP | 06269430 | 9/1994 | WO | WO9316629 | 9/1993 |
| JP | 06285048 | 10/1994 | WO | WO9403102 | 2/1994 |
| JP | 07001273 | 1/1995 | WO | WO9423643 | 10/1994 |
| JP | 07124138 | 5/1995 | WO | WO9502358 | 1/1995 |
| JP | 07136150 | 5/1995 | WO | WO9512349 | 5/1995 |
| JP | 03116259 | 6/1995 | WO | WO9516970 | 6/1995 |
| JP | 03116260 | 6/1995 | WO | WO9613208 | 5/1996 |
| JP | 07155311 | 6/1995 | WO | WO9616591 | 6/1996 |
| JP | 07155313 | 6/1995 | WO | WO9639927 | 12/1996 |
| JP | 03238813 | 7/1995 | WO | WO9736536 | 10/1997 |
| JP | 07171139 | 7/1995 | WO | WO9736538 | 10/1997 |
| JP | 03134144 | 9/1995 | WO | WO9749330 | 12/1997 |

| | | |
|---|---|---|
| WO | WO9809566 | 3/1998 |
| WO | WO9817174 | 4/1998 |
| WO | WO9818382 | 5/1998 |
| WO | WO9836681 | 8/1998 |
| WO | WO9843071 | 10/1998 |
| WO | WO9851212 | 11/1998 |
| WO | WO9857577 | 12/1998 |
| WO | WO9900053 | 1/1999 |
| WO | WO9932030 | 7/1999 |
| WO | WO9947039 | 9/1999 |
| WO | WO9963884 | 12/1999 |
| WO | WO0021438 | 4/2000 |
| WO | WO0028888 | 5/2000 |
| WO | WO0059374 | 10/2000 |
| WO | WO0113790 | 3/2001 |
| WO | WO0116577 | 3/2001 |
| WO | WO0117421 | 3/2001 |
| WO | WO0147426 | 3/2001 |
| WO | WO0140776 | 6/2001 |
| WO | WO0167946 | 9/2001 |
| WO | WO0176461 | 10/2001 |
| WO | WO0214793 | 2/2002 |
| WO | WO0235999 | 5/2002 |
| WO | WO02062213 | 8/2002 |
| WO | WO02074162 | 9/2002 |
| WO | WO02075289 | 9/2002 |
| WO | WO02085202 | 10/2002 |
| WO | WO03000125 | 1/2003 |
| WO | WO03001180 | 1/2003 |
| WO | WO03009750 | 2/2003 |
| WO | WO03011127 | 2/2003 |
| WO | WO03020129 | 3/2003 |
| WO | WO03039326 | 5/2003 |
| WO | WO03063697 | 8/2003 |
| WO | WO03073924 | 9/2003 |
| WO | WO2004000114 | 12/2003 |
| WO | WO2004006748 | 1/2004 |
| WO | WO2004069046 | 8/2004 |
| WO | WO2004075746 | 9/2004 |
| WO | WO2005002434 | 1/2005 |
| WO | WO2005009221 | 2/2005 |
| WO | WO2005010567 | 2/2005 |
| WO | WO2005010568 | 2/2005 |
| WO | WO2005020120 | 3/2005 |
| WO | WO2005053530 | 6/2005 |
| WO | WO2005065540 | 7/2005 |
| WO | WO2006039752 | 4/2006 |
| WO | WO2006064399 | 6/2006 |
| WO | WO2006110488 | 10/2006 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Barreto, Armando B., et al.; "Adaptive LMS Delay Measurement in dual Blood Volume Pulse Signals for Non-Invasive Monitoring," *IEEE*, pp. 117-120 (1997).

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Buschman, J.P., et al.; "Principles and Problems of Calibration of Fetal Oximeters," *Biomedizinische Technik*, vol. 42, pp. 265-266 (1997).

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Leahy, Martin J., et al.; "Sensor Validation in Biomedical Applications," *IFAC Modelling and Control in Biomedical Systems*, Warwick, UK; pp. 221-226 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (1997).

Plummer, John L., et al.; "Identification of Movement Artifact by the Nellcor N-200 and N-3000 Pulse Oximeters," *Journal of clinical Monitoring*, vol. 13, pp. 109-113 (1997).

Poets, C. F., et al.; "Detection of movement artifact in recorded pulse oximeter saturation," *Eur. J Pediatr.*; vol. 156, pp. 808-811 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Soto, Denise A.; "A Comparative Study of Pulse Oximeter Measurements: Digit Versus Earlobe," Master of Science Thesis, California State University Dominguez Hills, May 1997, 46 pgs.

"Smaller Product, Tighter Tolerances Pose Dispensing Challenges for Medical Device Manufacturer," *Adhesives Age*, pp. 40-41 (Oct. 1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Masin, Donald I., et al.; "Fetal Transmission Pulse Oximetry," *Proceedings $19^{th}$ International Conference IEEE/EMBS*, Oct. 30-Nov. 2, 1997; pp. 2326-2329.

Pickett, John, et al.; "Pulse Oximetry and PPG Measurements in Plastic Surgery," *Proceedings—$19^{th}$ International Conference—IEEE/EMBS*, Chicago, Illinois, Oct. 30-Nov. 2, 1997, pp. 2330-2332.

DeKock, Marc; "Pulse Oximetry Probe Adhesive Disks: a Potential for Infant Aspiration," *Anesthesiology*, vol. 89, pp. 1603-1604 (1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the $20^{th}$ Annual International conference of the IEEE Engineering in Medicine and Biology Society*, vol. 20, No. 6, pp. 3072-3075 (1998).

Ferrell, T.L., et al.; "Medical Telesensors," *SPIE*, vol. 3253, pp. 193-198 (1998).

König, Volker, et al.; "Reflectance Pulse Oximetry—Principles and Obstetric Application in the Zurich System," *Journal of Clinical Monitoring and Computing*, vol. 14, pp. 403-412 (1998).

Lutter, N., et al.; "Comparison of Different Evaluation Methods for a Multi-wavelength Pulse Oximeter," *Biomedizinische Technik*, vol. 43, (1998).

Nogawa, Masamichi, et al.; "A Novel Hybrid Reflectance Pulse Oximater Sensor with improved Linearity and General Applicability to Various Portions of the Body," *Proceedings of the $20^{th}$ Annual International Conference of the IEEE Engineering in Medicine and Biology Society*, vol. 20, No. 4, pp. 1858-1861 (1998).

Odagiri, Y.; "Pulse Wave Measuring Device," Micromechatronics, vol. 42, No. 3, pp. 6-11 (1998) (Article in Japanese—contains English summary of article).

Such, Hans Olaf; "Optoelectronic Non-invasive Vascular Diagnostics Using multiple Wavelength and Imaging Approach," *Dissertation*, (1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

East, Christine E., et al.; "Fetal Oxygen Saturation and Uterine Contractions During Labor," *American Journal of Perinatology*, vol. 15, No. 6, pp. 345-349 (Jun. 1998).

Hayes, Matthew J., et al.; "Quantitative evaluation of photoplethysmographic artifact reduction for pulse oximetry," *SPIE*, vol. 3570, pp. 138-147 (Sep. 1998).

Rhee, Sokwoo, et al.; "The Ring Sensor: a New Ambulatory Wearable Sensor for Twenty-Four Hour Patient Monitoring," *Proceedings of the 20th Annual International Conference of the IEEE Engineering in Medicine and Biology Society*, vol. 20, No. 4, pp. 1906-1909 (Oct. 1998).

Hayes, Matthew J., et al.; "Artifact reduction in photoplethysmography," *Applied Optics*, vol. 37, No. 31, pp. 7437-7446 (Nov. 1998).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Aoyagi, T., et al.; "Pulse Oximeters: background, present and future," *Neonatal Care*, vol. 13, No. 7, pp. 21-27 (2000) (Article in Japanese—contains English summary of article).

Edrich, Thomas, et al.; "Pulse Oximetry: an Improved in Vitro Model that Reduces Blood Flow-Related Artifacts," *IEEE Transactions on Biomedical Engineering*, vol. 47, No. 3, pp. 338-343 (Mar. 2000).

Goldman, Julian M.; "Masimo Signal Extraction Pulse Oximetry," *Journal of Clinical Monitoring and Computing*, vol. 16, pp. 475-483 (2000).

Hamilton, Patrick S., et al.; "Effect of Adaptive Motion-Artifact Reduction on QRS Detection," Biomedical Instrumentation & Technology, pp. 197-202 (2000).

Kaestle, S.; "Determining Artefact Sensitivity of New Pulse Oximeters in Laboratory Using Signals Obtained from Patient," *Biomedizinische Technik*, vol. 45 (2000).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Vicenzi, Martin N.; "Transesophageal versus surface pulse oximetry in intensive care unit patients," *Crit. Care Med.*; vol. 28, No. 7, pp. 2268-2270 (2000).

Yang, Boo-Ho, et al.; "Development of the ring sensor for healthcare automation," *Robotics and Autonomous Systems*, vol. 30, pp. 273-281 (2000).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Schulz, Christian Eric; "Design of a Pulse Oximetry Sensor Housing Assembly," California State University Master's Thesis, *UMI Dissertation Services*, UMI No. 1401306, (May 2000) 63 pages.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Belal, Suliman Yousef, et al.; "A fuzzy system for detecting distorted plethysmogram pulses in neonates and paediatric patients," *Physiol. Meas.*, vol. 22, pp. 397-412 (2001).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Cysewska-Sobusaik, Anna; "Metrological Problems With noninvasive Transillumination of Living Tissues," *Proceedings of SPIE*, vol. 4515, pp. 15-24 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Gosney, S., et al.; "An alternative position for the pulse oximeter probe," *Anaesthesia*, vol. 56, p. 493 (2001).

Kim, J.M., et al.; "Signal Processing Using Fourier & Wavelet Transform," pp. II-310-II-311 (2001).

Lopez-Silva et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Irie, A., et al.; "Respiration Monitors—Pulse Oximeters," *Neonatal Care*, vol. 15, No. 12, pp. 78-83 (2002) (Article in Japanese—contains English summary of article).

J. Hayoz, et al.; "World's First Combined digital Pulse Oximetry Pulse Oximetry and Carbon Dioxide Tension Ear Sensor", Abstracts, A6, p. S103. (2002).

J. Huang, et al.; "Low Power Motion Tolerant Pulse Oximetry," Abstracts, A7, p. S103. (2002).

Jopling, Michael W., et al.; "Issues in the Laboratory Evaluation of Pulse Oximeter Performance," *Anesth Analg*, vol. 94, pp. S62-S68 (2002).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Lang, et al.; "Signal Identification and Quality Indicator™ for Motion Resistant Pulse Oximetry," Abstracts, A10, p. S105. (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Asada, Harry H. et al., "A new ring sensor design for improved motion artifact reduction without circulatory interference," Progress Report No. 3-3, Oct. 1, 2001-Mar. 31, 2002, MIT Home Automation and Healthcare Consortium , pp. 1-45.

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Itoh, K., et al.; "Pulse Oximeter," Toyaku Zasshi (Toyaku Journal), vol. 25, No. 8, pp. 50-54 (2003) (Article in Japanese—contains English summary of article).

Johansson, A.; "Neural network for photoplethysmographic respiratory rate monitoring," *Medical & Biological Engineering & Computing*, vol. 41, pp. 242-248 (2003).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Matsui, A., et al.; "Pulse Oximeter," *Neonatal Care*, vol. 16, No. 3, pp. 38-45 (2003) (Article in Japanese—contains English summary of article).

Matthews, Nora S. et al.; "An evaluation of pulse oximeters in dogs, cats and horses," *Veterinary Anaesthesia and Analgesia*, vol. 30, pp. 3-14 (2003).

Nakagawa, M., et al.; "Oxygen Saturation Monitor," *Neonatal Monitoring*, vol. 26, No. 5, pp. 536-539 (2003) (Article in Japanese—contains English summary of article).

Pujary, C., et al.; "Photodetector Size Considerations in the Design of a Noninvasive Reflectance Pulse Oximeter for Telemedicine Applications," *IEEE*, pp. 148-149 (2003).

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lopez-Silva et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Lee, C.M., et al.; "Reduction of Motion Artifacts from Photoplethysmographic Recordings Using Wavelet Denoising Approach," *IEEE EMBS Asian-Pacific Conference on Biomedical Engineering*, Oct. 20-22, 2003; pp. 194-195.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Branche, Paul C., et al.; "Measurement Reproducibility and Sensor Placement Considerations in Designing a Wearable Pulse Oximeter for Military Applications," 2 pgs. (2004).

Crespi, F., et al.; "Near infrared oxymeter prototype for non-invasive analysis of rat brain oxygenation," *Optical Sensing, Proceedings of SPIE*, vol. 5459, pp. 38-45 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Johnston, W. S., et al.; "Effects of Motion Artifacts on helmet-Mounted Pulse Oximeter Sensors," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Mannheimer, Paul D., et al.; "The influence of Larger Subcutaneous Blood Vessels on Pulse Oximetry," *Journal of Clinical Monitoring and Computing*, vol. 18, pp. 179-188 (2004).

Nuhr, M., et al.: "Forehead SpO$_2$ monitoring compared to finger SpO$_2$ recording in emergency transport," *Anaesthesia*, vol. 59, pp. 390-393 (2004).

Reuss, James L.; "Factors Influencing Fetal Pulse Oximetry Performance," *Journal of clinical Monitoring and Computing*, vol. 18, pp. 13-14 (2004).

Spigulis, Janis, et al.; "Optical multi-channel sensing of skin blood pulsations," *Optical Sensing, Proceedings of SPIE*, vol. 5459, pp. 46-53 (2004).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Matsuzawa, Y., et al.; "Pulse Oximeter," *Home Care Medicine*, pp. 42-45 (Jul. 2004); (Article in Japanese—contains English summary of article).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Jovanov, E., et al.; "Reconflgurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Urquhart, C., et al.; "Ear probe pulse oximeters and neonates," *Anaesthesia*, vol. 60, p. 294 (2005).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

PCT/US2007/010603 International Search Report mailed Sep. 7, 2008.

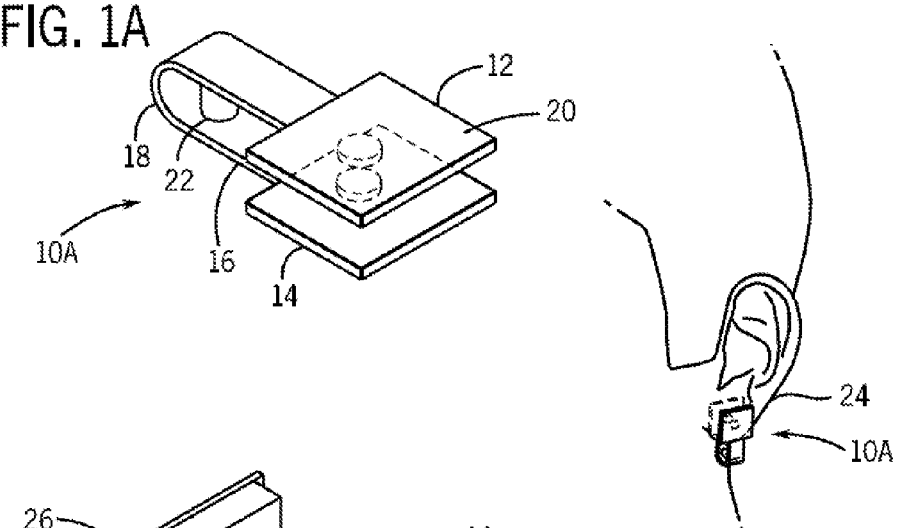
FIG. 1A
FIG. 1B
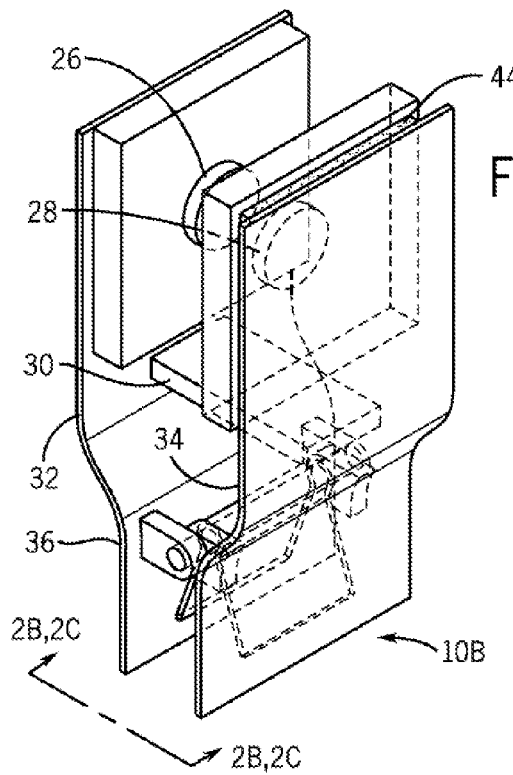
FIG. 2A
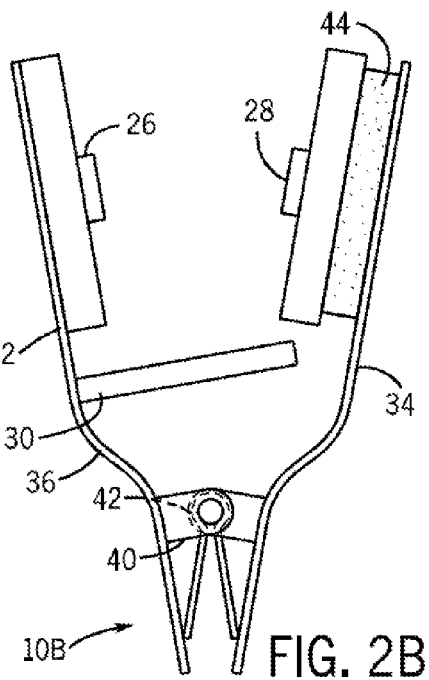
FIG. 2B

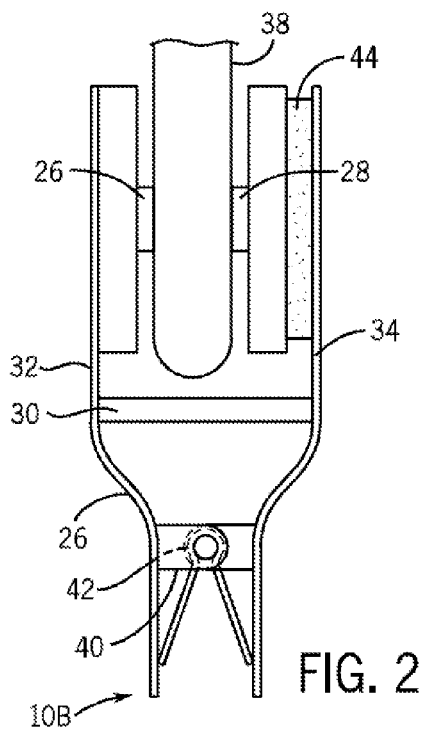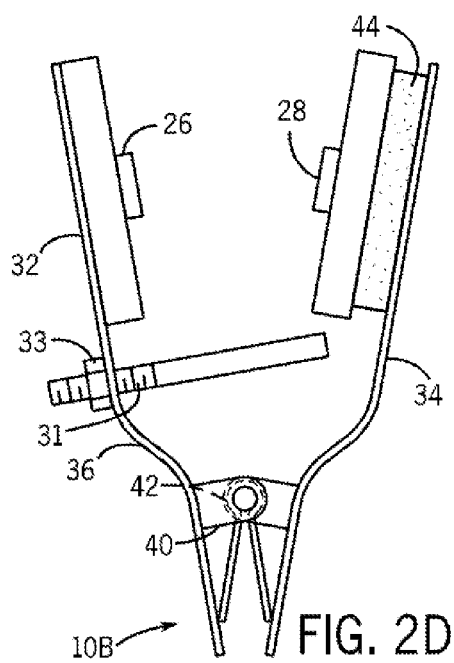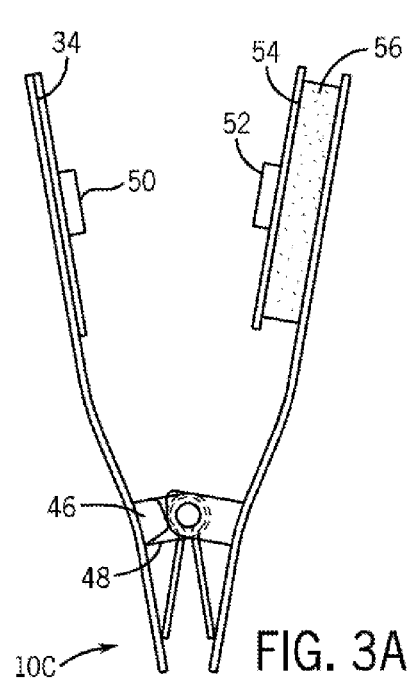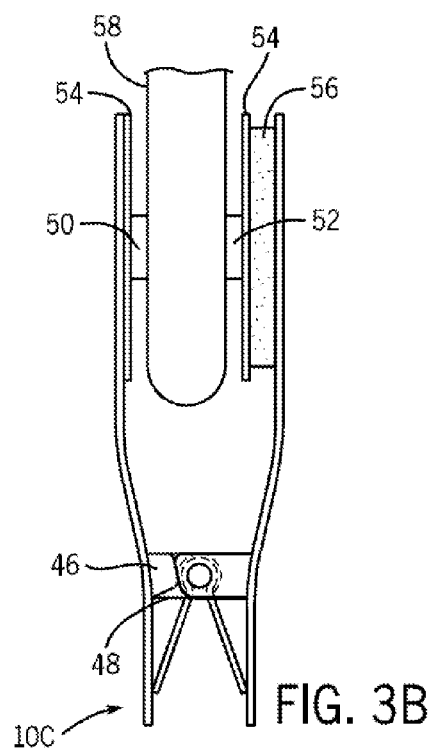

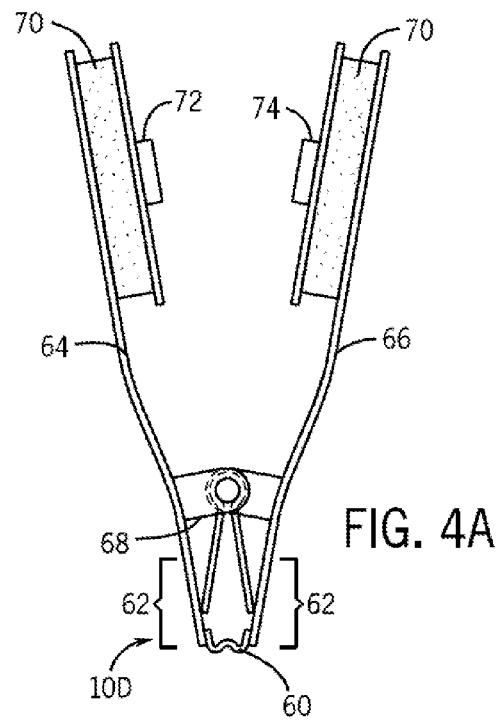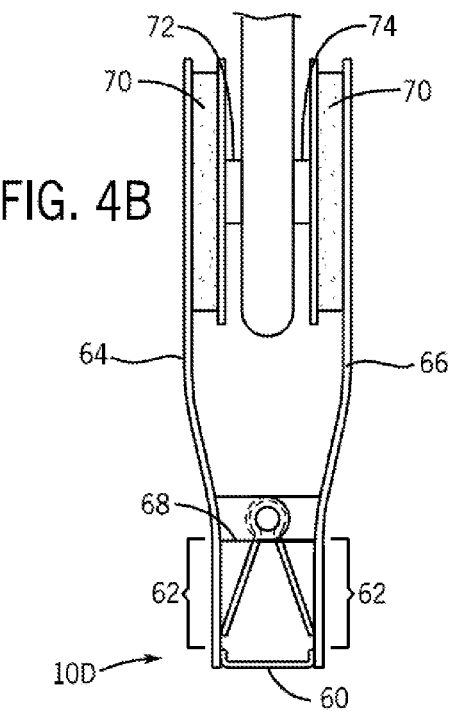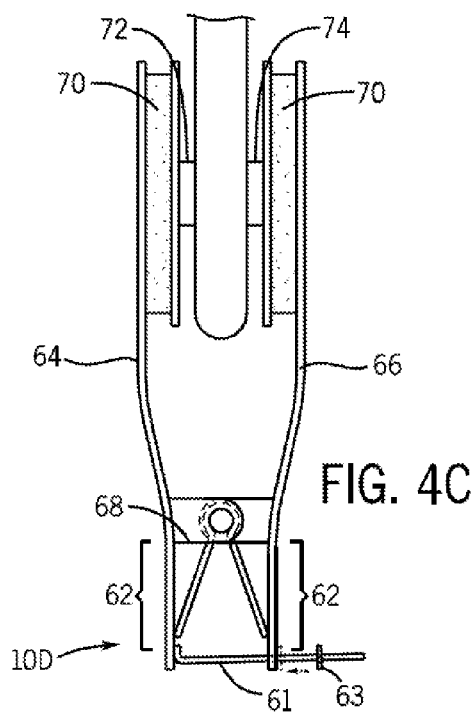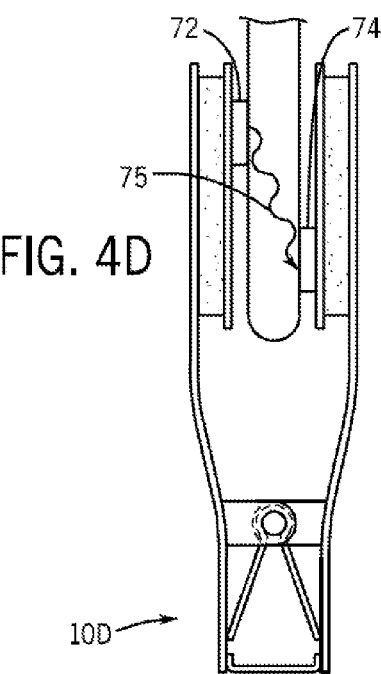

CLIP-STYLE MEDICAL SENSOR AND TECHNIQUE FOR USING THE SAME

CROSS-REFERENCE TO RELATED APPLICATIONS

This application is a continuation of U.S. patent application Ser. No. 11/415,717, filed May 2, 2006, the specification of which is incorporated by reference in its entirety herein for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Conventional pulse oximetry sensors are either disposable or reusable. In many instances, it may be desirable to employ, for cost and/or convenience, a reusable pulse oximeter sensor. Reusable sensors are typically semi-rigid or rigid devices that may be clipped to a patient. Unfortunately, reusable sensors may be uncomfortable for the patient for various reasons. For example, sensors may have angled or protruding surfaces that, over time, may cause discomfort. In addition, reusable pulse oximeter sensors may pose other problems during use. For example, lack of a secure fit may allow light from the environment to reach the photodetecting elements of the sensor, thus causing inaccuracies in the resulting measurement.

Because pulse oximetry readings depend on pulsation of blood through the tissue, any event that interferes with the ability of the sensor to detect that pulsation can cause variability in these measurements. A reusable sensor should fit snugly enough that incidental patient motion will not dislodge or move the sensor, yet not so tight that nonual blood flow to the tissue is disrupted. As sensors are worn for several hours at a time, an overly tight fit may cause local exsanguination of the tissue around the sensor. Exsanguinated tissue, which is devoid of blood, shunts the sensor light through the tissue, resulting in increased measurement errors.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body having a first portion and a second portion; a spring adapted to bias the first portion towards the second portion; a stopping element adapted to establish a minimum distance between the first portion and the second portion; and at least one sensing element disposed on the sensor body.

There is provided a sensor that includes: a sensor body having a first portion, a second portion; a spring adapted to bias the first portion towards the second; a substrate disposed on at least one of the fust portion or the second portion, wherein the substrate is adapted to move with at least one degree of freedom relative to the sensor body; and at least one sensing element disposed on the substrate.

There is also provided a pulse oximetry system that includes: a pulse oximetry monitor and a pulse oximetry sensor adapted to be operatively coupled to the monitor, the sensor comprising: a sensor body having a first portion and a second portion; a spring adapted to bias the first portion towards the second portion; a stopping element adapted to establish a minimum distance between the first portion and the second portion; and at least one sensing element disposed on the sensor body.

There is also provided a method of operating a sensor that includes: biasing a first portion and a second portion of a sensor body towards one another with a spring; and establishing a minimum distance between the first portion and the second portion with a stopper disposed on the sensor body.

There is also provided a method of manufacturing a sensor that includes: providing a sensor body having a first portion and a second portion; providing a spring adapted to bias the first portion towards the second portion; providing a stopping element adapted to establish a minimum distance between the first portion and the second portion; and providing at least one sensing element disposed on the sensor body.

BRIEF DESCRIPTION OF THE DRAWINGS

Advantages of the invention may become apparent upon reading the following detailed description and upon reference to the drawings in which:

FIG. 1A illustrates a perspective view of an exemplary sensor with a stopper and a flat spring according to the present invention;

FIG. 1B illustrates the sensor of FIG. 1A applied to a patient earlobe according to the present invention;

FIG. 2A illustrates a perspective view of an exemplary sensor with a rigid bar according to the present invention;

FIG. 2B illustrates a cross-sectional view of the open sensor of FIG. 2A;

FIG. 2C illustrates a cross-sectional view of the sensor of FIG. 2A applied to a patient's earlobe;

FIG. 3A illustrates a cross-sectional view of an open exemplary sensor with a stopper within a hinge according to the present invention;

FIG. 3B illustrates a cross-sectional view of the sensor of FIG. 3A applied to a patient's earlobe;

FIG. 4A illustrates a cross sectional view of an exemplary sensor with a strap according to the present invention;

FIG. 4B illustrates a cross-sectional view of the sensor of FIG. 4A applied to a patieht's earlobe;

FIG. 4C illustrates a cross sectional view of an alternative embodiment of the sensor of FIG. 4A with an offset emitter and detector;

DETAILED DESCRIPTION OF SPECIFIC EMBODIMENTS

Figure 5A:
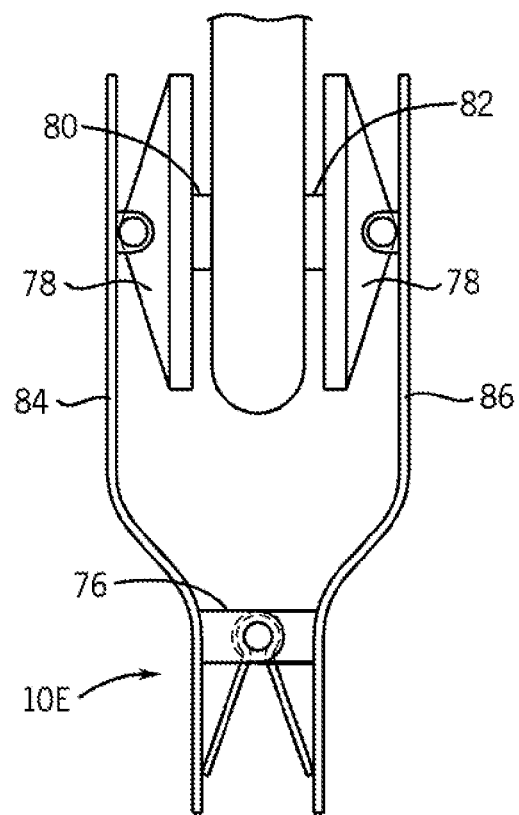
FIG. 5A illustrates a cross sectional view of an exemplary sensor with pivoting heads according to the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, motion-resistant pulse oximetry sensors are provided that reduce measurement error by applying limited and uniform pressure to the optically probed tissue. A clip-style sensor for pulse oximetry or other spectrophotometric uses is provided that has a compliant material disposed on the sensor to distribute the spring force of the clip to the tissue evenly when the sensor is applied to a patient. The clip-style sensor may also have a stopper that prevents the two portions of the clip from applying an excess of pressure to the patient's tissue. Alternatively, the clip-style sensor may allow the light emitting and detecting components of the sensor to tilt or otherwise move to accommodate the patient's tissue and to prevent overly tight gripping at the sensor placement site.

Pulse oximetry sensors are typically placed on a patient in a location that is normally perfused with arterial blood to facilitate measurement of the desired blood characteristics, such as arterial oxygen saturation measurement ($SpO_2$). The most common sensor sites include a patient's fingertips, toes, earlobes, or forehead, and clip-style sensors are most commonly used on patient digits, earlobes, or nose bridges. Regardless of the placement of the sensor 10, the reliability of the pulse oximetry measurement is related to the accurate detection of transmitted light that has passed through the perfused tissue. Hence, a sensor 10 that fits a patient securely may reduce movement of the sensor and/or infiltration of light from outside sources into the sensor, which may lead to more accurate pulse oximetry measurements.

There are several factors that may influence the tightness with which a sensor may grip a patient's tissue. It is desirable to affix the sensor 10 to the patient in a manner that does not exsanguinate the tissue, but that provides sufficient pressure to squeeze out excess venous blood. Excess venous blood congestion in the optically probed tissue may influence the relationship between the modulation ratio of the time-varying light transmission signals of the wavelengths transmitted and $SpO_2$. As venous blood has an increased concentration of deoxyhemoglobin as compared to arterial blood, its contribution to the pulse oximetry measurement may shift the wavelength of the detected light. Thus, the pulse oximetry sensor may measure a mixed arterial-venous oxygen saturation and detect differences in signal modulations unrelated to the underlying $SpO_2$ level. It is therefore desirable to reduce the contribution of excess venous blood to the pulse oximetry measurement by clipping a sensor to a patient's tissue with enough spring force to squeeze out excess venous blood.

On the other hand, a patient's tissue may suffer if clipped too tightly by a pulse oximetry sensor. In addition to causing patient discomfort, a sensor with excess gripping force in a hinge spring or other closing mechanism may squeeze both arterial and venous blood from a patient's tissue, causing the tissue to become exsanguinated. Light from a sensor's emitter that passes through such exsanguinated tissue may not be modulated by arterial blood, which may cause the resulting $SpO_2$ measurements to be artificially low. Thus, it is desirable to clip a sensor 10 to a patient's tissue tightly enough to reduce the amount of venous blood congestion, but not so tightly as to interfere with arterial blood perfusion.

In accordance with the present techniques, examples of clip-style sensors that apply limited, uniform pressure to a patient's tissue are disclosed. An exemplary sensor 10A adapted for use on a patient's earlobe is illustrated in FIG. 1A. The sensor has a first portion 12 and a second portion 14 that are applied to opposite sides of an earlobe. The sensor body 16 includes a flat spring 18 that may be used to connect the first portion 12 and the second portion 14. The first portion 12 and the second portion 14 may have a rigid outer layer 20.

The sensor 10A may also include a stopper 22 that limits the distance that the first portion 12 and the second portion 14 may move towards one another. Generally, it is envisioned that the stopper 22 be configured to allow the first portion 12 to move towards the second portion 14 such that they are not able to move past a minimum distance from one another that permits the sensor 10A to securely grip a patient's tissue. Such a minimum distance may generally be determined by the desired sensor placement site (e.g. nose, earlobe, or digit) and the size of the patient (e.g. child or adult). As the sensor 10A is applied to the patient's earlobe 24, the stopper 22 absorbs part of the spring force of the flat spring 18 to prevent the sensor 10A from gripping the tissue so tightly as to cause exsanguinations or discomfort. The stopper 22 may be permanently attached to the sensor body 16, or may be removable.

In an alternate embodiment, FIG. 2A depicts a perspective side view of a sensor 10B with a permanently attached rigid bar 30 acting as a stopper between a first portion 32 and a second portion 34 of a sensor body 36. An emitter 26 is disposed on the first portion 32 and a detector 26 is disposed on the second portion 34. The rigid bar 30 is permanently attached to the first portion 32 and moves away from the second portion 34 during the opening of the sensor 10B, as shown in the cross-sectional view of the open sensor 10B in FIG. 2B. However, it should be understood that the rigid bar 30 may alternatively be disposed on the second portion 34 in other embodiments. The rigid bar 30 as depicted is disposed on the first portion 32 of the sensor 10B in a region of the sensor body 36 that is free of intervening tissue when the sensor 10B is applied an earlobe 38, as shown in FIG. 2C. As the sensor 10B is closed, the rigid bar 30 contacts the second portion 34 and prevents further biasing of the first portion 32 towards the second portion 34. The first portion 32 and the second portion 34 may be connected by a hinge 40 with a spring 42. Thus, the rigid bar 30 restricts the range of motion of the hinge 40, such that the hinge 40 may only move the first portion 32 and the second portion 34 toward one another to a certain degree. Thus, the maximum spring force applied to the tissue is limited because the rigid bar 30 limits the force that the first portion 32 and the second portion 34 may exert against the earlobe 38.

When the sensor 10B is applied to the patient's earlobe 38, as shown in FIG. 2C, a resilient pad 44 absorbs part of the force of the spring 42 and distributes the remaining spring force to the earlobe 38 along the tissue-contacting surface of the sensor 10B. Thus, the total compression resistance of the resilient material is generally less than the force of the spring 42. The resilient pad may be any shock-absorbing material, including foam, silicone, or rubber. The sensor 10B thereby evenly distributes a limited force to the patient's tissue through use of a resilient pad 44, which spreads the force along the tissue-contacting surface.

In an alternate embodiment, depicted in FIG. 2D, the sensor 10B may include an adjustable bar 31 that may be threaded through an opening (not shown) in the sensor body 36. Thus, the length of the adjustable bar 31 may be increased by threading more length of the adjustable bar 31 through the sensor body 36. In such an embodiment, the minimum distance between the first portion 32 and the second portion 34 may be increased to accommodate the tissue of larger patients. Alternatively, smaller patients may require adjustment of the adjustable bar 31 such that more of the adjustable bar is threaded outside the sensor body 36 (i.e. not in the region between the first portion 32 and the second portion 34). Additionally, the sensor 10B may be applied to the patient, and a healthcare worker may adjust the length of the adjustable bar 31 until a desired amount of pressure on the tissue is achieved. In certain embodiments, the adjustable bar may be further secured by a nut 33 or other holding mechanism.

It is also envisioned that spring force of a hinge may be restricted by other mechanical structures. For example, in an alternative embodiment shown in FIG. 3A and FIG. 3B, a sensor 10C has a stopper 46 that is disposed within the mechanism of a hinge 48 to restrict rotational motion, thus preventing the hinge 48 from exerting maximum pressure to the tissue when sensor 10C is applied to a patient's earlobe 58. The stopper 46 may be a rigid material that is designed to mechanically block the motion of the hinge 48.

As depicted, the emitter 50 and the detector 52 are disposed on a thin substrate 54. The substrate 54 may be any suitable material, including plastic or woven cloth, and may be rigid or flexible. The substrate 54 may be disposed on the tissue-contacting side of a resilient pad 56. In certain embodiments, it may be advantageous to employ a flexible substrate 54, which may conform more closely to a patient's tissue when the sensor 10C is applied. In other embodiments, a more rigid substrate 54 may absorb more of the spring force of the hinge 48, and thus may prevent the sensor 10C from exerting excess pressure on the tissue.

Alternatively, as shown by the embodiment illustrated in FIGS. 4A-D, a sensor 10D may have a flexible but inelastic strap 60, such as a plastic or metal strap, disposed on the handle end 62 of the sensor body, connecting the first portion 64 and the second portion 66. When the sensor 10D is open, the strap 60 is slack. When the sensor 10D is closed, such as when the sensor 10D is applied to a patient, as shown in FIG. 4B, the strap 60 is drawn taut, thus preventing the hinge 68 from moving the first portion 64 and the second portion 66 closer than a distance dictated by the length of the strap 60.

As depicted, the sensor 10D has resilient pads 70 disposed on the tissue-contacting sides of the first portion 64 and the second portion 66 of a sensor. The use of a resilient pad 70 on both the first portion 64 and the second portion 66 provides greater compression resistance against the spring force of the hinge 68 than only a single resilient pad. Additionally, the spring force is evenly distributed along the tissue-contacting surface that holds both the emitter 72 and the detector 74 against the tissue. Thus, a sensor 10D may be used in conjunction with a relatively strong spring. This may be advantageous in situations in which an ambulatory patient may require the sensor 10D to fit securely enough to withstand dislodgement in response to everyday activity.

In an alternate embodiment, FIG. 4C illustrates a sensor 10D with an adjustable strap 61. The adjustable strap 61 may be threaded through an opening (not shown) in the sensor body. When an appropriate length of the adjustable strap is disposed between the first portion 64 and, the second portion 66 to provide the desired pressure on a patient's tissue, the adjustable strap 61 may be held in place by a clamp 63. As more length of the adjustable strap 61 is released into the region between the first portion 64 and the second portion 66, the sensor 10D is able to close more tightly over the tissue. Alternatively, a healthcare worker may pull the adjustable strap 61 through the sensor body such that the length of adjustable strap 61 between the first portion 64 and the second portion 66 is decreased, and as a result the sensor 10D would exert less pressure on the tissue.

Clip-style sensors as provided herein are often used on a patient's earlobes, which may have fewer vascular structures as compared to a digit. To maximize the transmission of light through well-perfused capillary structures, an alternative embodiment of the sensor 10D is depicted in which the emitter 72 and detector 74 are offset from each other, so that they are not directly opposite. This causes the light emitted by the emitter 72 to pass through more blood-perfused tissue to reach the detector 74. As such, the light has a greater opportunity to be modulated by arterial blood in a manner which relates to a blood constituent. FIG. 4D illustrates that the configuration of the sensor 10D provides a longer light transmission path through the tissue, as indicated by arrow 75.

Figure 5B:
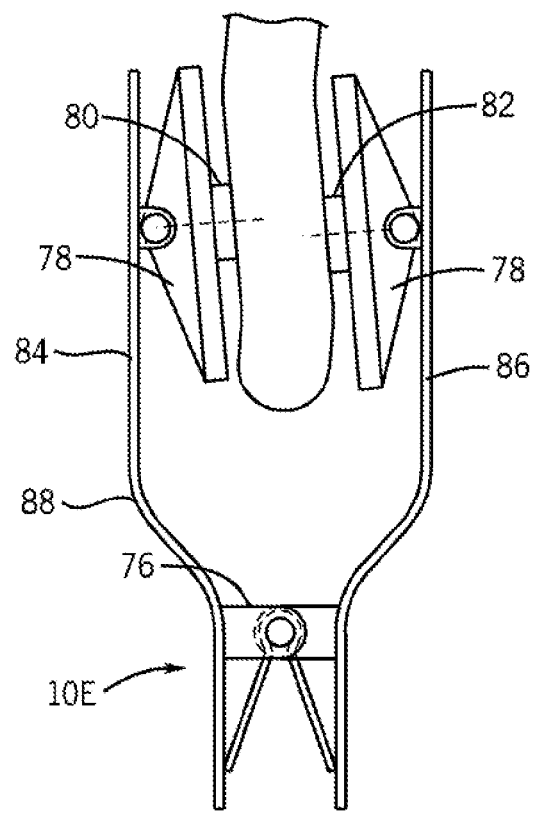
FIG. 5B illustrates a cross-sectional view of the sensor of FIG. 5A applied to a patient's earlobe.

FIG. 5A and FIG. 5B depict an embodiment of a sensor 10E in which part of the spring force of a hinge 76 is absorbed by pivoting heads 78, upon which an emitter 80 and a detector 82 are disposed. The pivoting heads 78 are disposed on a first portion 84 and a second portion 86 of the sensor 10E. The first portion 84 and the second portion 86 are connected by the hinge 76. Pivoting heads are disposed on the tissue-contacting side of the first portion 84 and the second portion 86. As FIG. 5B illustrates, the pivoting heads 78 may tilt relative to the sensor body 88 in order to accommodate the contours of the patient's tissue. In certain embodiments, the pivoting heads 78 may also include resilient pads (not shown) that distribute the spring force of the hinge 76 along the tissue-contacting surface of the sensor 10E. In other embodiments, the sensor 10E may also include a stopper or stopping mechanism as described herein.

In an alternate embodiment (not shown), an adhesive material is applied to the tissue-contacting surface of the sensor 10 to enhance the securing of the sensor 10 to the tissue. The use of an adhesive material may improve the contact of the sensor to the appendage, and limit the susceptibility to motion artifacts. In addition, the likelihood of a gap between the sensor body and the skin is avoided.

In certain embodiments, it is contemplated that the spring force of the hinge (e.g. 40, 48, 68, or 78) or other closing mechanism, such as a flat spring (e.g. flat spring 18), has sufficient pressure so that it exceeds the typical venous pressure of a patient, but does not exceed the diastolic arterial pressure. A sensor 10 that applies a pressure greater than the venous pressure will squeeze excess venous blood from the optically probed tissue, thus enhancing the sensitivity of the sensor to variations in the arterial blood signal.

Since the pressure applied by the sensor is designed to be less than the arterial pressure, the application of pressure to the tissue does not interfere with the arterial pulse signal. Typical venous pressure, diastolic arterial pressure and systolic arterial pressure are less than 10-35 mmHg, 80 mmHg, and 120 mmHg, respectively. These pressures may vary because of the location of the vascular bed and the patient's condition. In certain embodiments, the sensor may be adjusted to overcome an average pressure of 15-30 mmHg. In other embodiments, low arterial diastolic blood pressure (about 30 mmHg) may occur in sick patients. In such embodiments, the sensor 10 may remove most of the venous pooling with light to moderate pressure (to overcome about 15 mmHg). It is contemplated that removing venous blood contribution without arterial blood exsanguination may improve the arterial pulse signal.

Figure 6:
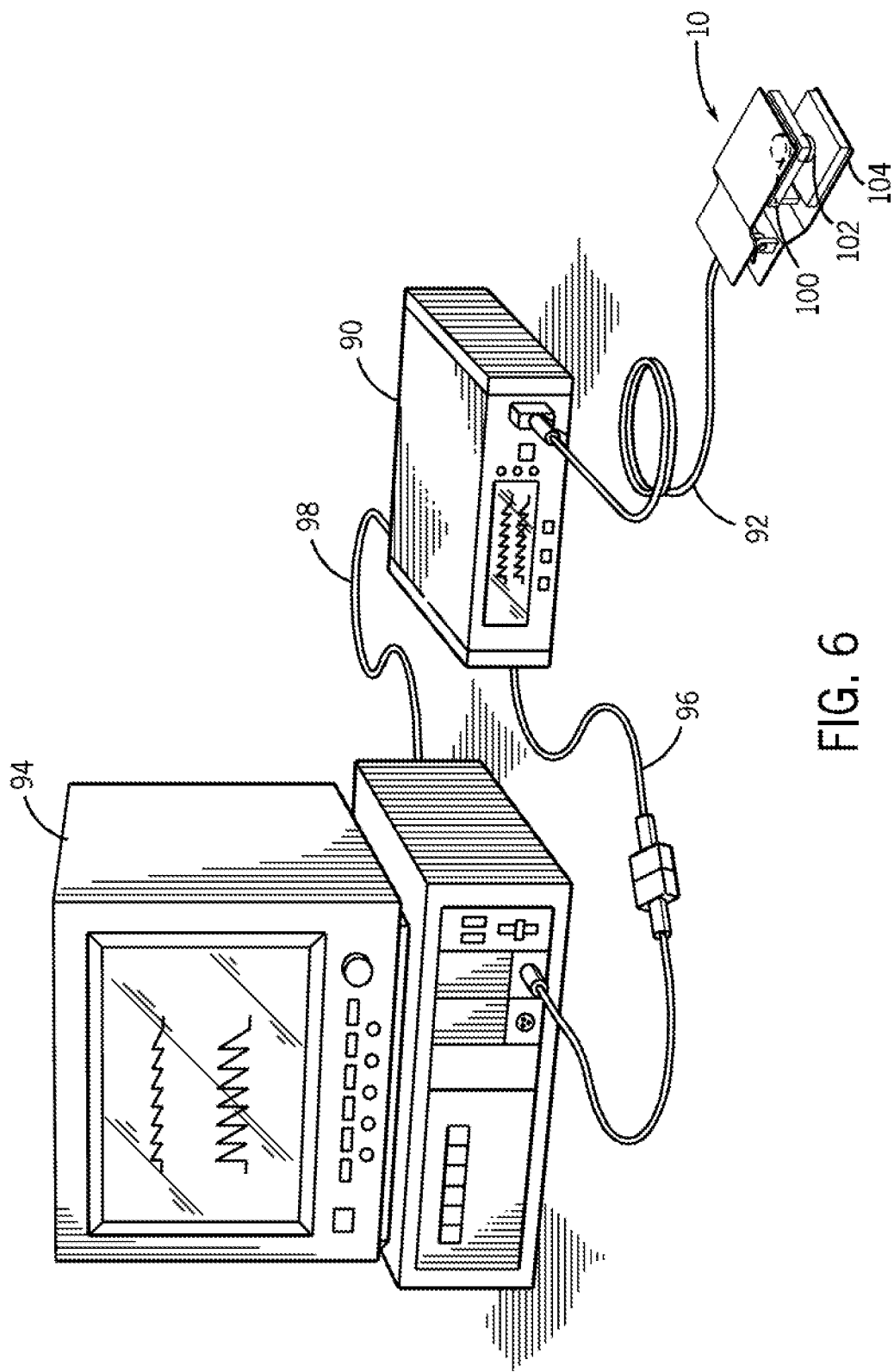
FIG. 6 illustrates a pulse oximetry system coupled to a multi-parameter patient monitor and a sensor according to embodiments of the present invention.

The exemplary sensors described above, illustrated generically as a sensor 10, may be used in conjunction with a pulse oximetry monitor 90, as illustrated in FIG. 6. It should be appreciated that the cable 92 of the sensor 10 may be coupled to the monitor 90 or it may be coupled to a transmission device (not shown) to facilitate wireless transmission between the sensor 10 and the monitor 90. The monitor 90 may be any suitable pulse oximeter, such as those available from Nellcor Puritan Bennett Inc. Furthermore, to upgrade conventional pulse oximetry provided by the monitor 90 to provide additional functions, the monitor 90 may be coupled to a multi-parameter patient monitor 94 via a cable 96 connected to a sensor input port or via a cable 98 connected to a digital communication port.

The sensor 10 includes an emitter 100 and a detector 102 that may be of any suitable type. For example, the emitter 100 may be one or more light emitting diodes adapted to transmit one or more wavelengths of light in the red to infrared range, and the detector 102 may be a photodetector selected to receive light in the range or ranges emitted from the emitter 100. For pulse oximetry applications using either transmission or reflectance type sensors, the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The emitter 100 and the detector 102 may be disposed on a sensor body 104, which may be made of any suitable material, such as plastic, foam, woven material, or paper. Alternatively, the emitter 100 and the detector 102 may be remotely located and optically coupled to the sensor 10 using optical fibers. In the depicted embodiments, the sensor 10 is coupled to a cable 92 that is responsible for transmitting electrical and/or optical signals to and from the emitter 100 and detector 102 of the sensor 10. The cable 92 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 100 and detector 102 that are typically placed on opposing sides of the sensor site. If the sensor site is a fingertip, for example, the sensor 10 is positioned over the patient's fingertip such that the emitter 100 and detector 102 lie on either side of the patient's nail bed. In other words, the sensor 10 is positioned so that the emitter 100 is located on the patient's fingernail and the detector 102 is located 180° opposite the emitter 100 on the patient's finger pad. During operation, the emitter 100 shines one or more wavelengths of light through the patient's fingertip and the light received by the detector 102 is processed to determine various physiological characteristics of the patient. In each of the embodiments discussed herein, it should be understood that the locations of the emitter 100 and the detector 102 may be exchanged. For example, the detector 102 may be located at the top of the finger and the emitter 100 may be located underneath the finger. In either arrangement, the sensor 10 will perform in substantially the same manner.

Reflectance type sensors generally operate under the same general principles as transmittance type sensors. However, reflectance type sensors include an emitter 100 and detector 102 that are typically placed on the same side of the sensor site. For example, a reflectance type sensor may be placed on a patient's fingertip or forehead such that the emitter 100 and detector 102 lie side-by-side. Reflectance type sensors detect light photons that are scattered back to the detector 102.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. Rather, the invention is to cover all modifications, equivalents, and alternatives falling within the spirit and scope of the invention as defined by the following appended claims.

What is claimed is:

1. A sensor adapted to be applied to a patient's tissue comprising:
   a sensor body having a first portion and a second portion biased towards one another by a spring force;
   a resilient material disposed on the first portion of the sensor body; at least one sensing element disposed on a substrate, wherein the substrate is associated with an opposing surface of the resilient material such that the resilient material is between the substrate and the sensor body; and
   a stopping element configured to contact the first portion and the second portion when the sensor is applied to the patient's tissue, wherein the stopping element is capable of establishing a minimum distance between the first portion and the second portion and wherein a portion of the spring force is configured to be absorbed by the resilient material when the sensor is applied to the patient's tissue such that the sensor body applies a pressure that is sufficient to overcome a venous pressure but not an arterial pressure of the patient.

2. The sensor, as set forth in claim 1, wherein the stopping element comprises a rigid bar.

3. The sensor, as set forth in claim 1, wherein the stopping element comprises a plug.

4. The sensor, as set forth in claim 1, wherein the stopping element comprises a substantially inelastic strap.

5. The sensor, as set forth in claim 1, wherein the first portion and the second portion are coupled at an end of the sensor.

6. The sensor, as set forth in claim 1, wherein the resilient material comprises a foam.

7. The sensor, as set forth in claim 1, wherein the substrate is flexible.

8. The sensor, as set forth in claim 1, wherein the sensing element comprises an emitter and a detector.

9. The sensor, as set forth in claim 8, wherein the emitter comprises a light-emitting diode and the detector comprises a photodetector.

10. The sensor, as set forth in claim 1, wherein the sensor comprises at least one of a pulse oximetry sensor, a sensor for measuring a water fraction, or a combination thereof.

11. The sensor, as set forth in claim 1, wherein the sensor is configured to operate in transmission mode.

12. A pulse oximetry system comprising:
a pulse oximetry monitor; and
a pulse oximetry sensor adapted to be operatively coupled to the monitor, the sensor comprising:
a sensor body having a first portion and a second portion biased towards one another by a spring force;
a resilient material disposed on the first portion of the sensor body; at least one sensing element disposed on a substrate, wherein the substrate is associated with an opposing surface of the resilient material such that the resilient material is between the substrate and the sensor body; and
a stopping element configured to contact the first portion and the second portion when the sensor is applied to a patient's tissue, wherein the stopping element is capable of establishing a minimum distance between the first portion and the second portion and wherein a portion of the spring force is configured to be absorbed by the resilient material when the sensor is applied to the patient's tissue such that the sensor body applies a pressure that is sufficient to overcome a venous pressure but not an arterial pressure of the patient.

13. The pulse oximetry system, as set forth in claim 12, wherein the sensing element comprises an emitter and wherein a detector is disposed on the second portion.

14. The pulse oximetry system, as set forth in claim 13, wherein detector is disposed on the second portion such that the emitter and the detector are not opposite each other.

15. A sensor adapted to be applied to a patient's tissue comprising:
a sensor body having a first portion and a second portion biased towards one another by a spring force;
a stopping element configured to contact the first portion and the second portion when the sensor is applied to the patient's tissue, wherein the stopping element is capable of establishing a minimum distance between the first portion and the second portion that results in the sensor body applying a pressure to the patient's tissue that is sufficient to overcome a venous pressure but not an arterial pressure of the patient; and
at least one sensing element associated with the first portion of the sensor body.

16. The sensor, as set forth in claim 15, wherein the sensor is configured to be applied to an ear.

17. The sensor, as set forth in claim 15, wherein the sensor is configured to be applied to a finger.

18. The sensor, as set forth in claim 15, wherein the stopping element comprises a rigid bar or a plug.

19. The sensor, as set forth in claim 15, wherein the sensor is a pulse oximetry sensor.

20. The sensor, as set forth in claim 15, wherein the sensor is configured to operate in transmission mode.

\* \* \* \* \*